US005913834A

United States Patent [19]

Francais

[11] Patent Number: 5,913,834

[45] Date of Patent: Jun. 22, 1999

[54] SYSTEM FOR IMPARTING SENSORY EFFECTS ACROSS A MOTHER'S ABDOMEN TO A FETUS AND MONITORING EFFECTS ON THE FETUS

[76] Inventor: Caramia Francais, 2808 Los Posas Cir., Camarillo, Calif. 93012

[21] Appl. No.: 09/094,369

[22] Filed: Jun. 9, 1998

Related U.S. Application Data

[63] Continuation-in-part of application No. 08/276,418, Jul. 18, 1994, Pat. No. 5,764,776, which is a continuation-in-part of application No. 08/143,981, Nov. 4, 1993, Pat. No. 5,491, 756.

[51] Int. Cl.[6] .......... A61B 5/00

[52] U.S. Cl. .......... 600/591

[58] Field of Search .......... 600/551, 587, 600/591, 595, 310, 476; 381/24, 90

[56] References Cited

U.S. PATENT DOCUMENTS

| | | | |
|---|---|---|---|
| 4,438,772 | 3/1984 | Slavin | 128/715 |
| 4,798,539 | 1/1989 | Haney et al. | 434/319 |
| 4,934,998 | 6/1990 | Thomas | 600/27 |
| 5,109,421 | 4/1992 | Fox | 381/90 |

*Primary Examiner*—Max Hindenburg
*Attorney, Agent, or Firm*—Robert J. Schaap

[57] ABSTRACT

A system for generating and delivering various types of sensory effects to a fetus or so-called "fetal child" through a mother's abdomen and simultaneously allowing for the monitoring of the effects on the fetus. In a preferred embodiment, the system relies upon the generation of light of various intensities, wavelengths or color to provide certain types of stimulation to the fetus. Vibrations or magnetic effects can also be transmitted across the abdomen wall of the mother to the fetus. The system utilizes a belt which is worn about the abdomen of the mother and includes transducers located in the region of the fetal child for imparting the desired sensory effect. A stethoscope or like device can be mounted in and carried by the belt and is designed for juxtaposition to the abdomen and in proximity to the fetus. The stethoscope head piece can be worn by the mother to determine the effects of the stimulus on the fetus.

20 Claims, 7 Drawing Sheets

SYSTEM FOR IMPARTING SENSORY EFFECTS ACROSS A MOTHER'S ABDOMEN TO A FETUS AND MONITORING EFFECTS ON THE FETUS

RELATED APPLICATION

This application is a continuation-in-part of my U.S. patent application Ser. No. 08/276,418, filed Jul. 18, 1994, now U.S. Pat. No. 5,764,776 and which is, in turn, a continuation-in-part of U.S. patent application Ser. No. 143,981 filed Nov. 4, 1993 entitled "System for Delivering Sound to and Monitoring Effects on a Fetus" now U.S. Pat. No. 5,491,756, dated Feb. 13, 1996).

BACKGROUND OF THE INVENTION

1. Field of the Invention

This invention relates in general to certain new and useful improvements in systems for generating and delivering various types of sensory effects to a fetal child through a mother's abdomen and more particularly, to a system of the type stated which also allows for the generation of the sensory effect and transmission across the abdomen wall, as well as means for monitoring for the effects on the fetal child.

2. Brief Description of the Related Art

There have been numerous attempts to impart sounds, such as music and the like to a fetus during gestation. Prior art attempts to impart any type of sensory excitation to the fetus were usually rudimentary and unsophisticated.

In U.S. Pat. No. 5,109,421, dated Apr. 28, 1992, entitled "Fetal Speaker System And Support Belt For Maternal Wear" there is provided a more sophisticated system for generating and imparting sound to a fetus. In this prior art device, a belt is provided and supports speakers for imparting sound through the abdomen wall to the fetal child. While this device is effective, it has been found to be lacking in certain respects, not the least of which is the fact that the belt itself did not provide sufficient support to hold transducers, sound generators and the like.

It has also been recognized that there is a possibility that other forms of sensory excitation can be generated and transmitted to the fetus through the wall of the abdomen of the mother. However, there are no effective techniques for applying other types of sensory effects.

It is believed that imparting of various types of sensory effects to the fetus can be effective in creating a bond between the fetus and the mother. The sound, if properly selected, can provide a soothing effect to the fetus. For that matter, a light of a selected proper frequency, capable of at least some transmission across the abdomen wall, may also have a desirable effect on the fetus. In addition, the fetus may also find vibration effects imparted across the abdomen wall to be desirable. Not only does this create a more pleasurable gestation period for the fetus, but it also helps to create a bond between the mother and the fetus.

It has also been recognized in the art that applications of radiation, as well as physical actions such as vibration, for example, of various types across the abdomen of a mother can be and is received by the fetus and has a sensory type effect on the fetus. Moreover, the fetus can and frequently does respond to the application of the sensory effects. Thus, a type of communication is achieved between the mother and the fetus when these sensory effects are transmitted to the fetus. The fetus can express its pleasure or displeasure at the type of sensory effects by the physical movement of the fetus within the mother's abdomen.

The applicant has now discovered that it is possible to apply certain types of electromagnetic radiation, such as light, magnetic effects and the like across the abdomen wall to the fetus from a harness-type device which can be worn by the mother and which is essentially portable in construction.

The applicant has also discovered that various types of light effects clearly have an effect upon the fetus. It has now been established that laser light, for example, is one form of light to which the fetus is clearly sensitive. The laser light, in particular, is collimated and can, when of sufficient intensity, does impact on the fetus. The applicant has theorized and believes that the pineal gland of the fetus, even though in a developmental stage, will respond to this light energy much in the same manner as a pineal gland of a living individual is effected by the presence of light or lack of light on an individual, even when that individual is sleeping.

It has been found that in all cases, it is desirable to also provide for monitoring the effects of any type of sensory excitation on the fetus. It is possible to determine if the fetus reacts negatively to one form of sensory excitation or favorably to another form of excitation. In this way, the mother can selectively apply that excitation form favorable to the fetus.

In addition, it is recognized that many mothers find pregnancy to be uncomfortable, if not painful, due to the fact that they are carrying a substantial additional amount of weight in their abdomen. This almost necessarily creates strains on the back, as well as other parts of the skeletal muscular system. While there is no effective way to reduce the extra weight being carried by the mother, the deleterious effects can be mitigated to some extent by applying sensory effects to the mother. Vibration, and/or heat are oftentimes effective for this purpose. Thus, in any device in which sensory effects are imparted to a fetus, it may also be desirable to impart certain sensory effects to the mother.

OBJECTS OF THE INVENTION

It is, therefore, one of the primary objects of the present invention to provide a system for generating and imparting sensory effects to a fetus through a mother's abdomen and which also allows for monitoring of the effects on the fetus.

It is another object of the present invention to provide a system of the type stated which is capable of generating and imparting various types of sensory effects, such as light effects, magnetic effects, vibrational effects or the like, all of which can be imparted to the fetus cross the abdomen wall of the mother.

It is a further object of the present invention to provide a system of the type stated which can be adapted so as to interchangeably provide different types of transducers for generating different type of effects to be transmitted to the fetus.

It is still another object of the present invention to provide a light source of desired intensity, color and wavelength which can be transmitted across a mother's abdomen to a fetus in order to create a desired sensory effect on the fetus.

It is also an object of the present invention to provide a system for generating and imparting sensory effects to the fetus and which is highly reliable in its operation and highly effective in creating a desired effect on the fetus.

It is an additional object of the present invention to provide a system for generating and imparting sensory effects to a fetus and also for generating and providing sensory effects to a mother to aid the mother during the gestation period.

It is yet another object of the present invention to provide a system of the type stated which can be manufactured at a relatively low unit cost and which is highly reliable in operation.

With the above and other objects in view, my invention resides in the novel features of form, construction, arrangement and combination of parts presently described and pointed out in the claims.

BRIEF SUMMARY OF THE DISCLOSURE

Generally speaking, the present invention relates to a system for generating and imparting various types of sensory effects, and particularly electromagnetic radiation-type sensory effects to a fetus (often referred to as a "fetal child") through the mother's abdomen wall and which also allows for monitoring of the effects on the fetal child. The system of the invention also is effective for providing various sensory effects to the mother in order to aid in overcoming some of the discomforts associated with pregnancy.

The system for generating and imparting sensory effects of the present invention adopts some of the basic principles utilized in U.S. Pat. No. 5,109,421, but constitutes a significant advance thereover in that it not only solves many of the problems which had arisen in prior art sound systems, but also allows for transmitting of other types of sensory effects. Furthermore, the system of the present invention also allows for the important aspect of monitoring the effects on the fetus.

The system for generating and imparting various types of sensory effects comprises a belt sized for wearing disposition about the waist of a woman user. That belt may adopt the form of belt which is now described and claimed in my previously identified U.S. Patent Applications. That belt typically is designed with an enlarged frontal portion which extends over a substantial surface area of the lower abdomen of the woman user and provides greater support for the transducers and sensory effect generators, as well as the monitoring equipment.

In one of the preferred embodiments, sound generation is usually employed. In this case, at least one speaker is carried by and mounted on the belt. Preferably, a pair of spaced-apart speakers are mounted on and carried by the belt and located in juxtaposition to the abdomen and in proximity to the fetal child. Thus, sound can be imparted to the fetal child across the wall of the abdomen.

The sound generator may adopt any form of the type described in my aforesaid co-pending patent application. As a simple example, a radio, a tape player or compact disc player or a so-called "Walkman" unit may be mounted in and carried by the belt. This sound generator is capable of generating sounds of the type to be imparted to the fetal child and has one or more outputs connected to the one or more speakers.

Speakers may also be located for external transmission of sound, if desired. However, in accordance with the invention, the primary focus is upon the transmission of sensory effects to the fetus.

In one embodiment of the invention, the system is designed to generate light of various intensities and/or frequencies for imparting across the wall of the abdomen to the fetus. While the fetus itself may not have yet developed sight capability, the applicant has, nevertheless, determined that light radiation does, in fact, have some effect on the fetus. This is particularly the case when the frequency, and hence color, of the light changes and when the intensity of the light changes. For example, it is possible to provide a type of strobing effect which allows the light to be rapidly turned on and off. In other cases, it is possible to change the frequency, and hence the color, of the light.

In accordance with the present invention, the applicant has now been able to define various types of light sources which are effective in creating desired sensory effects on the fetus and in generating responses from the fetus. In particular, one of these light sources relies upon the use of laser light. Moreover, and in each case, the applicant has developed a means to enable generation of the light from a light generator carried on the belt or other harness arrangement which is worn by the mother. In particular, one form of carbon dioxide laser light source has been developed for generating of laser light across the abdomen of the mother and directed to the fetus.

The applicant has also found in accordance with the present invention that the light which is generated is not necessarily limited to the visible light frequency spectrum. Thus, for example, both ultraviolet light and infrared light at opposite ends of the visible frequency spectrum also have an effect on the fetus. For some reason, and even though the fetus may not actually observe the non-visible light energy, as such, the pineal gland of the fetus, and even though in the development stage, nevertheless responds to that light.

In another embodiment of the invention, the invention relies upon the use of magnetic effects which are generated and imparted across the wall of the abdomen to the fetus. These magnetic effects can be either generated by permanent magnets or by electromagnets. In the case of permanent magnets, the magnets, such as alnico magnets, are mounted on and contained within pockets in the belt. The magnetic effects are normally created by the magnet and the effects thereof are imparted to the fetus through the abdomen wall.

Where stronger magnetic effects are desired, electromagnetic effects can be generated by use of a simple electromagnetic transducer. A battery source of power may be carried by the belt and the electromagnetic transducers are connected to the battery source of power. A switch means is also provided for energizing and de-energizing the electromagnetic transducers.

In still another embodiment of the invention, vibrational effects can be created and transmitted across the abdomen wall to the fetus. In this case, the vibrational effects would be created by some type of vibration-generating device as, for example, a conventional massage unit. Electric power is again provided by a battery unit or battery pack carried on the belt which is worn by the mother and is conducted to the vibration generator through electrical conductors.

In one of the important aspects of the invention, the effects of these various types of sensory excitations are monitored. For this purpose, a conventional stethoscope can be used. A suitable stethoscope sensor may be mounted in and carried by the belt to be located in juxtaposition to the mother's abdomen. The stethoscope sensor would, of course, be located in proximity to the fetal child to enable listening to the sounds generated by the fetal child in the mother's abdomen.

In a preferred embodiment, a sound conductor extends from the stethoscope sensor and has a connector for coupling to a stethoscope earpiece, so that the mother can monitor the effects of the sound on the fetal child. In this case, the stethoscope earpiece would be worn by the mother or other user of the system for listening to the sounds generated by the fetal child.

The present invention also envisions the use of other types of monitoring equipment. As a simple example, a heart rate monitor can be mounted on the belt with a sensor similarly located adjacent the abdomen of the mother and in proximity to the fetal child.

It is believed that in accordance with the present invention, the heart rate of the fetus may be a function of the effects which are imparted to the fetus. For example, where the fetus responds more favorably to soft music or to certain types of vibration or to a certain type of heat, these conditions can be noted and reapplied to the fetus at a later date. Otherwise, if the fetus responds negatively to certain types of sensory excitation, then the mother can avoid the imparting of that sensory excitation in the future.

It has also been established that the physical activity of the fetal child, as, for example, kicking, may be a result of the application of various sensory effects across the fetus and imparted to the fetal child. This is, again, another parameter for determining the effects of the sensory excitations upon the fetal child.

To the extent that any of the monitoring equipment requires electrical power, this equipment can be powered from the same source of electrical power, such as the batteries which are mounted on or carried by the belt.

The belt or other harness used in accordance with the present invention can also be provided with the devices for applying certain excitations to the mother. Thus, for example, a heating element can be mounted in the belt and located in juxtaposition to either the abdomen or the back of the mother. In like manner, vibratory mechanisms may also be mounted in the belt to literally apply vibration to the back of the mother and aid in overcoming back pain as a result of carrying the fetus.

This invention possesses many other advantages and has other purposes which will be made more fully apparent from a consideration from a consideration of the forms in which it may be embodied. These forms are show in the drawings forming part of and accompanying the present specification. They will now be described in detail for purposes of illustrating the general principles of the invention, but it is to be understood that the detailed description and the accompanying drawings are not to be taken in a limiting sense.

BRIEF DESCRIPTION OF THE DRAWINGS

Figure 1:
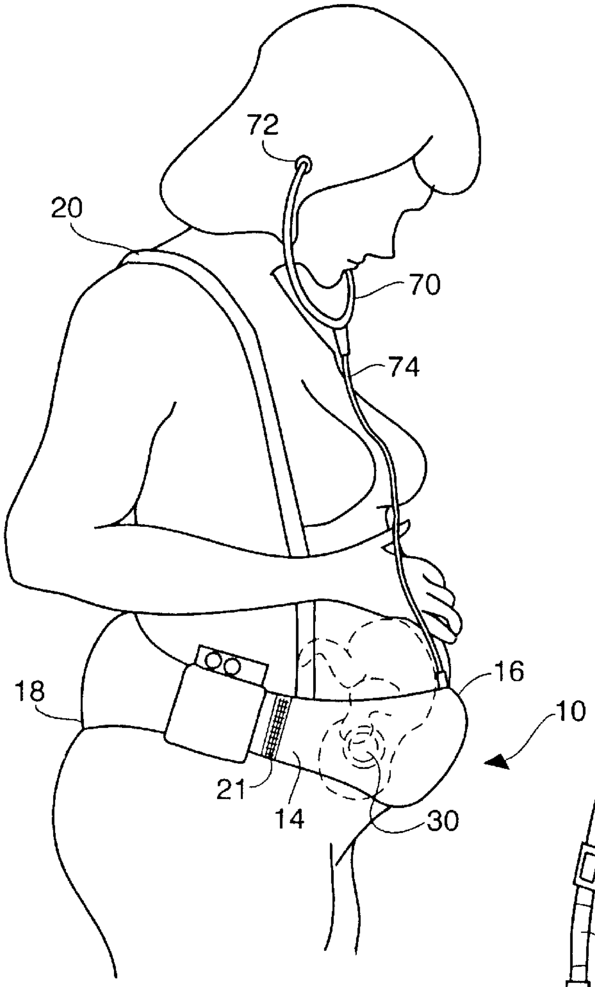
Figure 2:
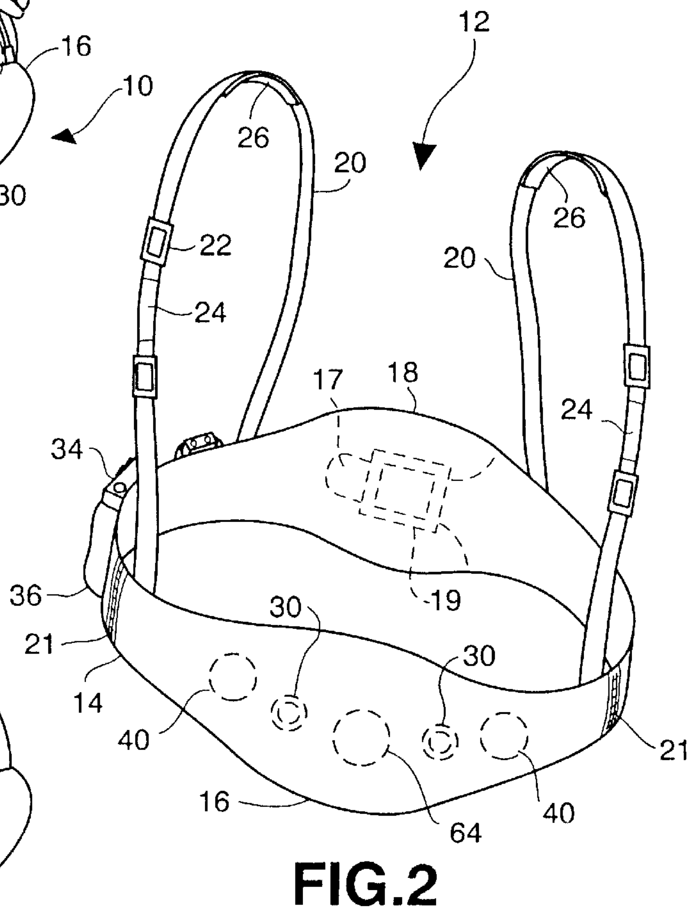
Figure 3:
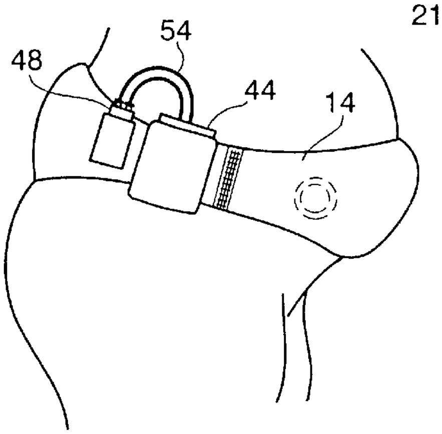
Figure 4:
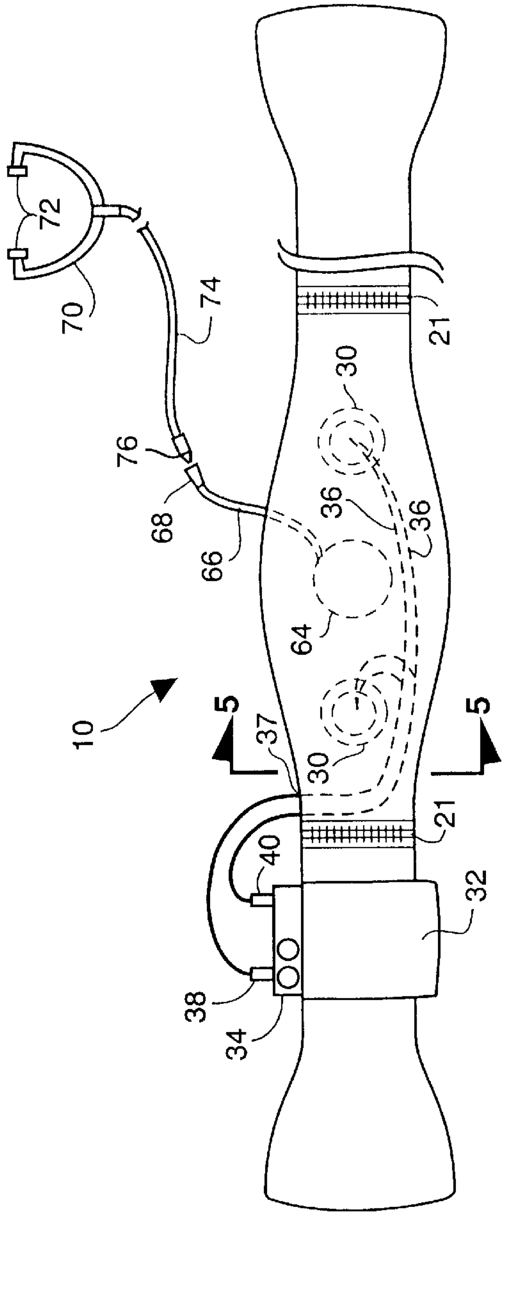
Figure 5:
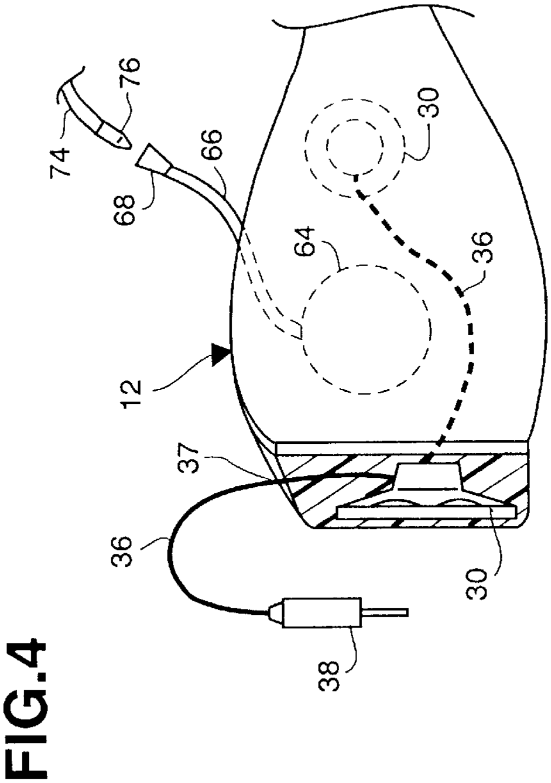
Figure 6:
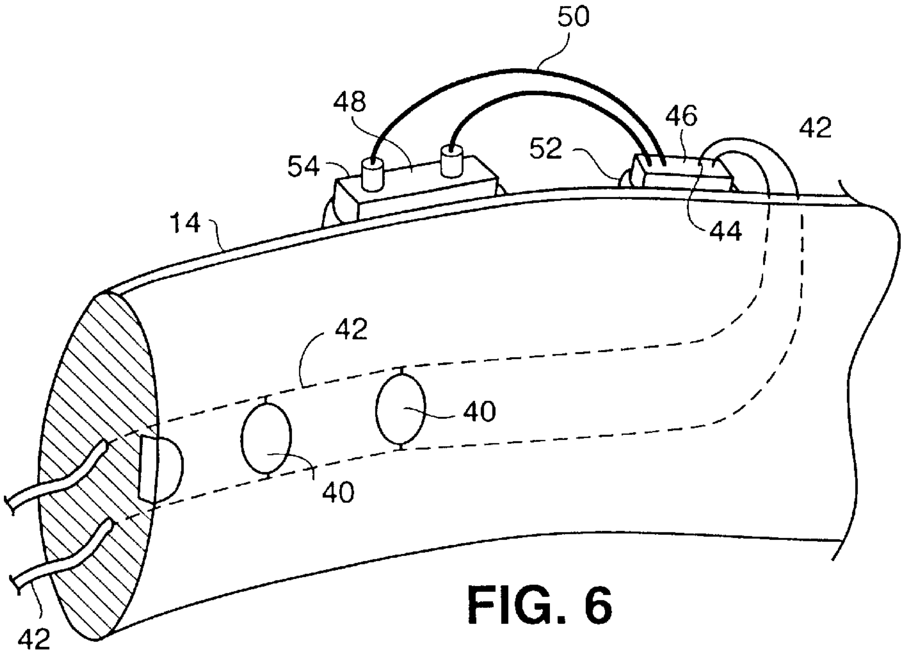
Figure 7:
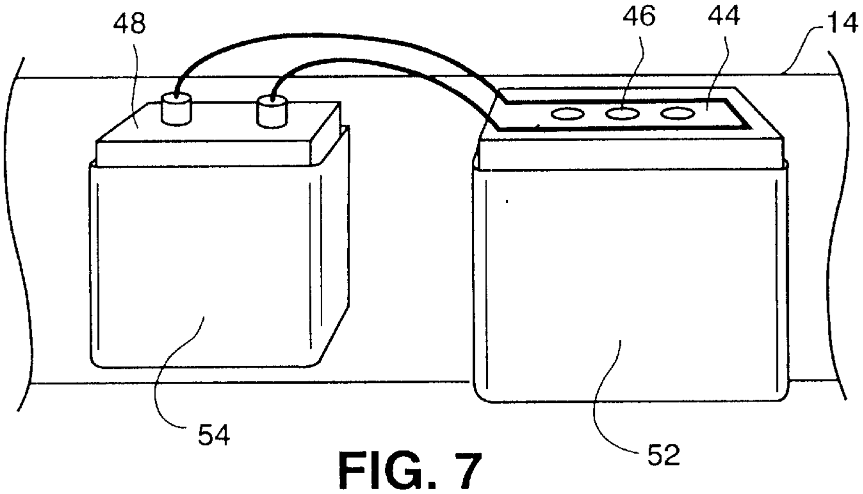
Figure 9:
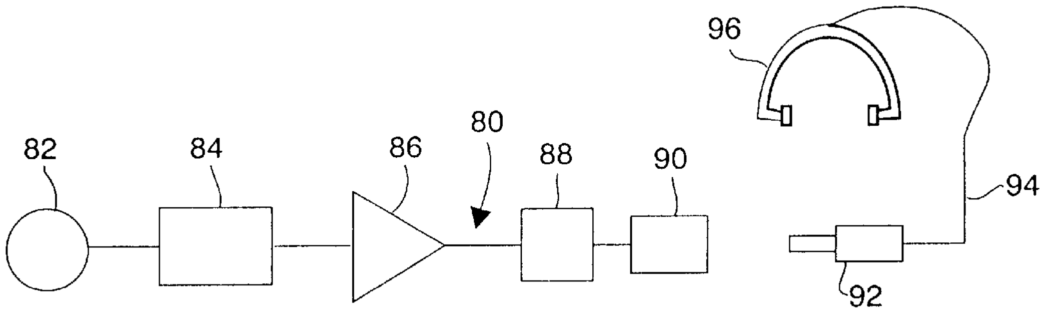
Figure 8:
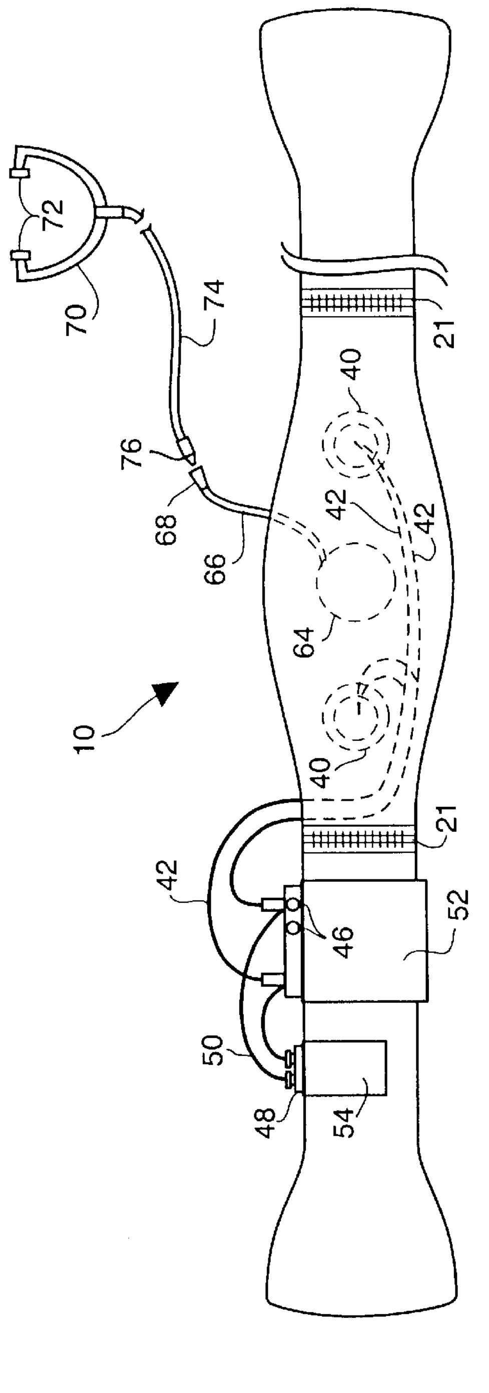
Figure 12:
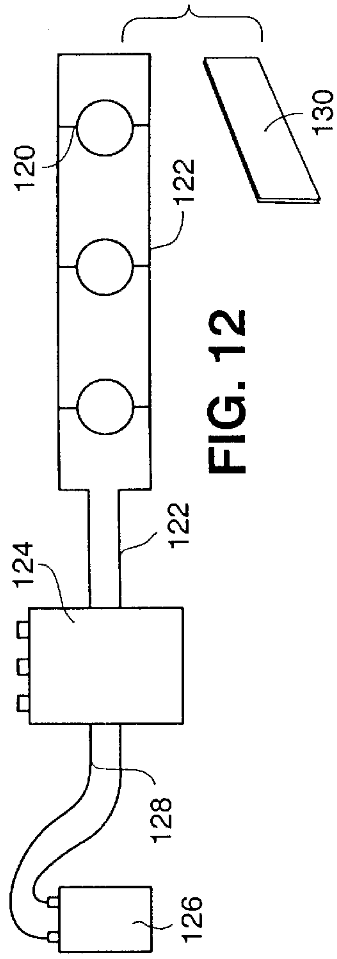
Figure 11:
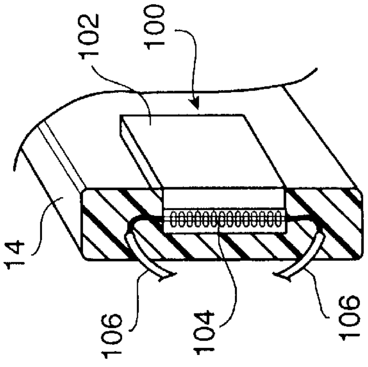
Figure 10:
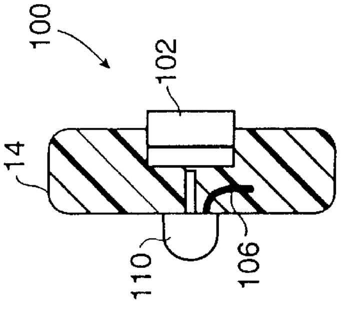
Figure 13:
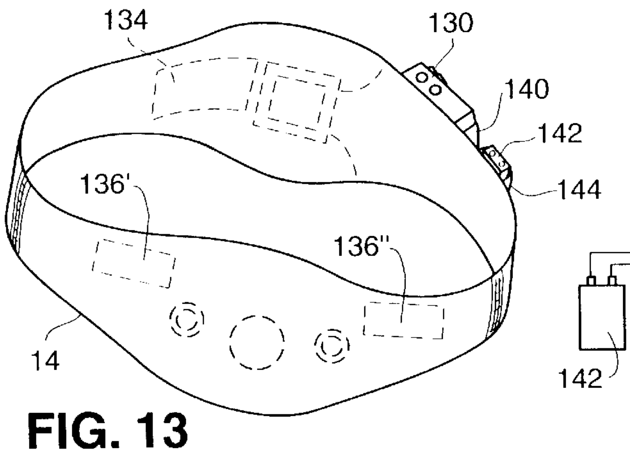
Figure 14:
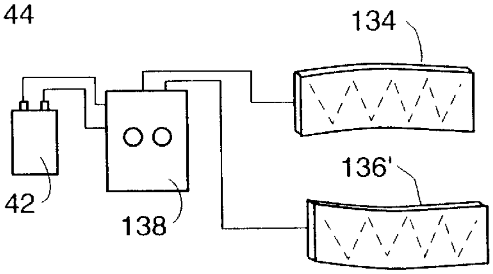
Figure 15:
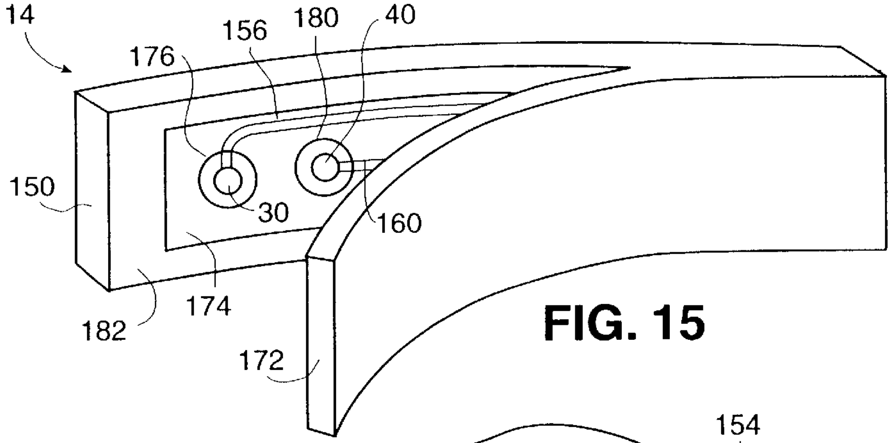
Figure 16:
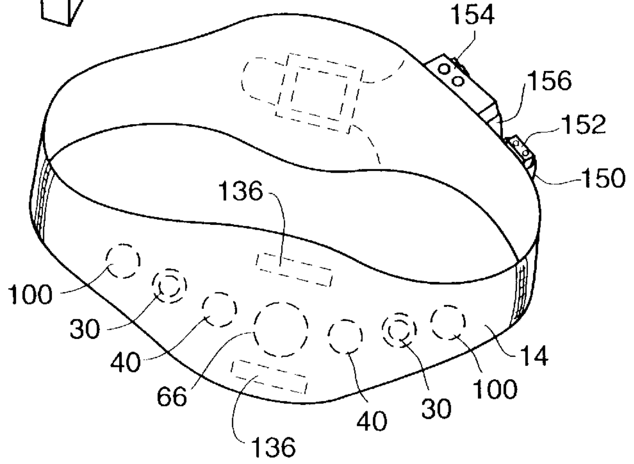
Figure 17:
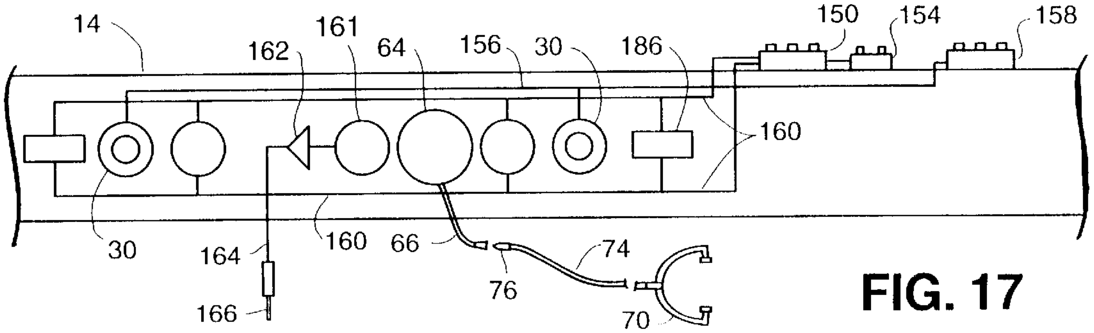
Figure 18:
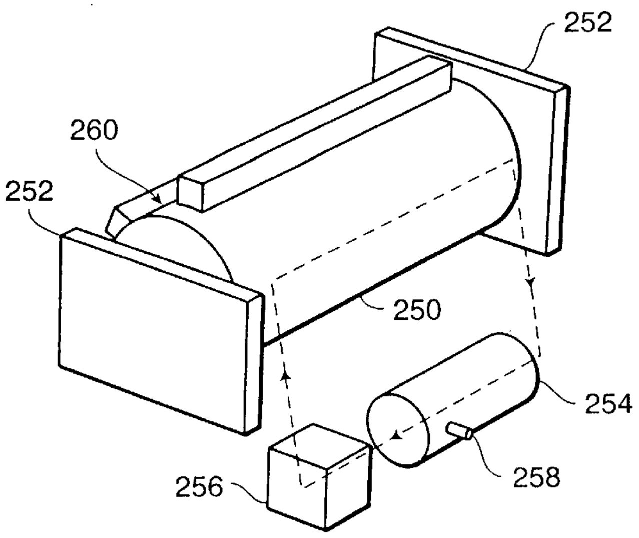
Figure 19:
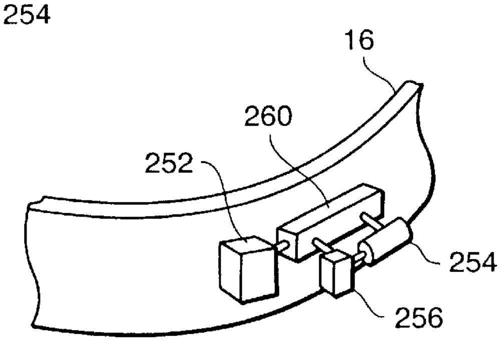
Figure 20:
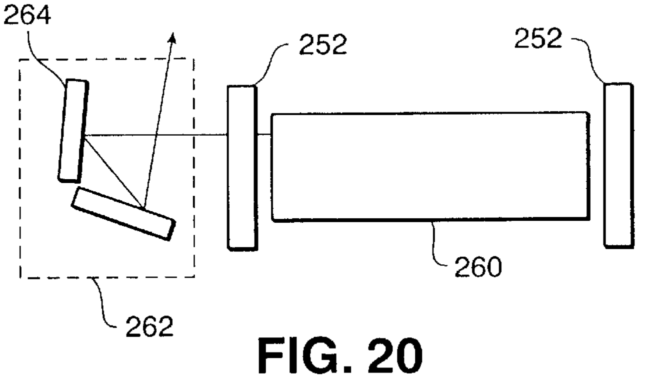
Figure 21:
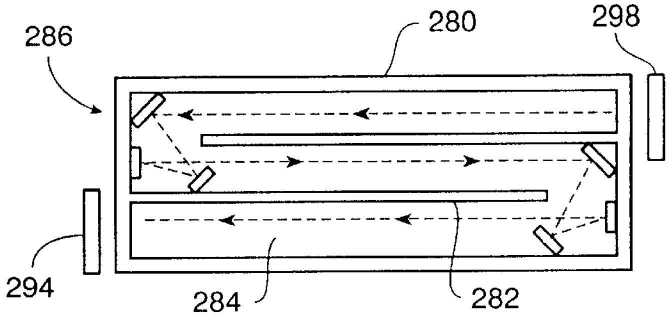
Figure 22:
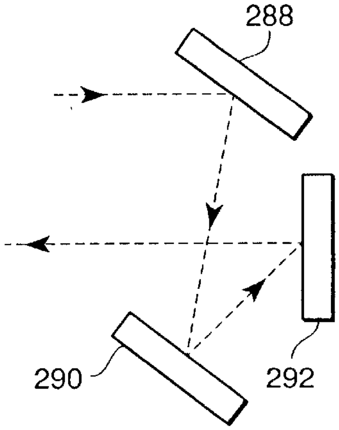
Figure 23:
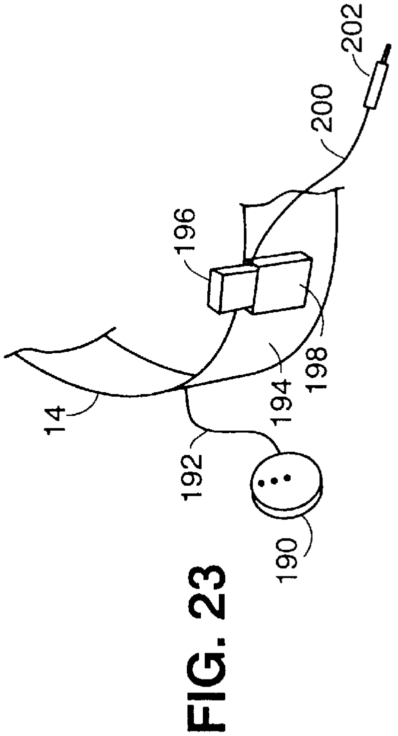
Figure 24:
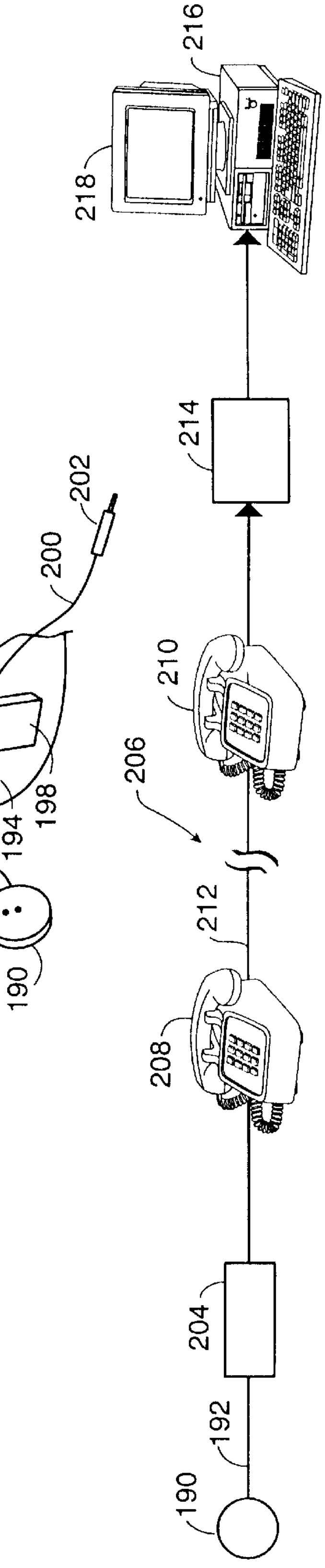
Figure 25:
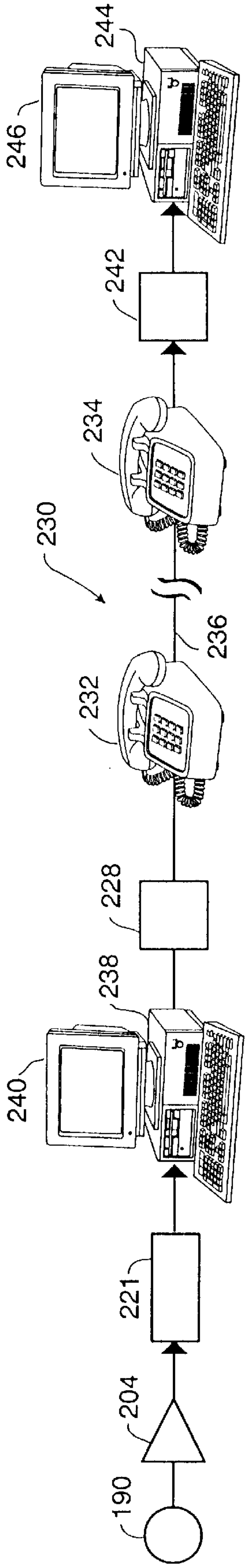

Having thus described the invention in general terms, reference will now be made to the accompanying drawings in which:

FIG. 1 is a perspective view of a system for generating and imparting sensory excitations across the abdomen wall of a mother to a fetus and showing a harness-type arrangement along with transducers for generating and imparting sensory effects;

FIG. 2 is a front perspective view of the system of FIG. 1 and specifically showing details of the harness-type arrangement;

FIG. 3 is a side elevational view of the harness-type arrangement forming part of a slightly modified form of system of the invention on the abdomen of a pregnant woman;

FIG. 4 is a front elevational view of the belt forming part of the harness-type arrangement and showing the use of sound sensory excitation;

FIG. 5 is a fragmentary plan view, partially in section of the embodiment of the invention of FIG. 4;

FIG. 6 is a fragmentary perspective view, partially in section, and showing connections of lighting devices to a control unit and a battery source of power;

FIG. 7 is a perspective view of the opposite side of the belt showing the control unit and battery of FIG. 6;

FIG. 8 is a front elevational view of the belt forming part of the harness of the invention utilizing light sensory excitation;

FIG. 9 is a schematic electrical view showing a portion of the electrical components used in fetal monitoring forming part of the system of the present invention;

FIG. 10 is a sectional view taken through the belt and showing the use of a vibrator mechanism;

FIG. 11 is a fragmentary perspective view, partially in section, of the system of FIG. 10;

FIG. 12 is a schematic electrical circuit view showing the components used with vibrators as the means for generating excess sensory excitation;

FIG. 13 is a perspective view of another modified form the belt using heating elements therein;

FIG. 14 is a schematic view showing some of the electrical circuitry used in operating heating elements forming part of the system of the invention;

FIG. 15 is a fragmentary perspective view in partially exploded form and showing a portion of the components and a means for mounting in a belt of the present invention;

FIG. 16 is a perspective view showing a large number of the sensory excitation devices mounted in a belt forming part of the harness-type arrangement;

FIG. 17 is a electrical circuit schematic view showing electrical connection of some of the components forming part of the present invention;

FIG. 18 is a perspective view, partially in schematic form, and showing one form of laser light generating device which can be used for causing sensory excitation upon a fetus;

FIG. 19 is a fragmentary perspective view showing the embodiment of FIG. 18 on a belt arrangement;

FIG. 20 is a schematic top plan view showing a redirecting of a laser light through a light directing mechanism to a fetus;

FIG. 21 is a sectional view through the light generating device of FIG. 18 showing a folded wave path;

FIG. 22 is a schematic view showing an arrangement of mirrors forming part of the folded light path used in FIG. 21;

FIG. 23 is a fragmentary perspective view showing one means for measuring information about a fetus or a mother and transmitting the same;

FIG. 24 is a schematic view showing one form of information transmitting system for purposes of transmitting information initially measured in acoustic form; and FIG. 25 is a schematic view showing another form of information transmitting system for transmitting information in digital electrical format.

DETAILED DESCRIPTION OF PREFERRED EMBODIMENTS

Referring now in more detail and by reference characters to the drawings which illustrate several practical embodiments of the present invention, 10 designates a system for generating and imparting sensory excitation to a fetus or so-called "fetal child" through the abdomen wall of the mother. The system 10 comprises a harness arrangement 12 which includes a belt 14 sized to extend around the abdomen of the mother. The belt 14 is constructed so that it has an enlarged frontal section 16 and an enlarged rear section 18.

By reference to FIG. 2, it can be observed that the enlarged frontal section 16 and, for that matter, the enlarged rear section 18, are both enlarged in the sense that they have a greater overall vertical dimension. In this way, it has been found that a belt with non-constant vertical dimension, particularly in the front and rear portions thereof, tends to provide a greater support to the mother who is wearing the harness 12 of the invention. In this case, it has been found that little support is actually provided on the sides and therefore, the sides are of reduced thickness.

In order to facilitate ease of wearing, the belt 14 is provided with a terminal end section 17 which fits within a belt buckle 19. Furthermore, it has been found in connection with the present invention that the terminal section 17 and the buckle 19 should be located at the rear portion of the belt in order to allow for some expansion of the belt as the fetus grows and the mother's abdomen expands. For this purpose, elastic strips 21 may also be formed on the sides of the belt in order to provide some degree of expansion. It should also be understood that other means for adjustably sizing the belt, such as the use of Velcro strips or the like could also be employed. The elastic strips 21 are preferably positioned toward the side of the belt so that they are, in effect, rearward of the speakers and other transducers. In this way, expansion of the mother's abdomen will not result in a changing of the position of the sensory transducers (hereinafter described) with respect to the fetal child.

In addition to the foregoing, and in order to provide greater support for the mother wearing this harness 12, the harness 12 is provided with a pair of suspender straps 20, as also best illustrated in FIGS. 1 and 2. The suspender straps 20 are also provided with buckles 22 for adjustably sizing the overall length of each of the suspender straps 20. Furthermore, if desired, these suspender straps 20 could be provided with elastic portions 24. These elastic portions 24 also allow for some individual stretching when the mother changes her position.

The suspender straps 20 should be connected to the belt so that they are adjustably securable to the belt at selected positions along the length of the belt. Thus, as the mother's abdomen expands, the belt is opened to a larger loop and the suspender straps can be moved outwardly. For this purpose, a series of buttons or other fasteners (not shown) may be provided on the belt for releasably securing the lower end of the suspender straps.

The underside of the suspender straps 20, particularly in the shoulder regions, are provided with soft pads 26 in order to provide wearing comfort to the mother. These shoulder pads 26 may be formed of a soft felt-like material so as to reduce the abrasive effect of a conventional pair of straps.

The belt 14 is preferably formed of a leather material, although any other type of material, such as a woven fabric or the like, could be used. Various rubber materials or foam materials could be used. A preferred rubber material which can be used is a neoprene rubber. However, leather is preferred inasmuch as it has some structural integrity and also provides for the necessary rigidity to hold speakers and a sound generator, as hereinafter described. The suspender straps 20 may also be formed of leather although, again, other materials may similarly be employed.

The belt 14 is provided with the buckle 19 for opening and closing the belt 14 in order to position the belt 14 around the waist of the user as also shown in FIGS. 1 and 2. Further, the belt 14 and the buckles 19 may be cooperatively designed so as to be adjustable in position.

The belt 14 is designed to carry one or more transducers and power sources, as may be required, at the option of the user. In this respect, the belt 14 could be provided with available pockets or the like in order to receive and hold one or more of the transducers. In this way, the user of the system can add the selected type of transducer at will. Otherwise, the belt 14 could be constructed to hold only a pre-selected number of transducers and perhaps, monitors.

In essentially all embodiments of the sensory excitation system, sound generating equipment will probably be used, since this is an important type of sensory effect to be provided to the fetal child. In the sound generating system there will be speakers 30 for imparting sound to the child fetus. The exact means for mounting the speakers 30 within the belt 14 is not critical and any conventional mechanism for mounting the speakers 30 may be employed. In the case of the present invention, the speakers 30 are fitted within recesses formed in the belt 14 and project to and through the interior surface of the belt 14. However, the outer surface of the speakers 30 is at least flush with the inner surface of the belt 14. In this way, the speakers 30 will be juxtaposed to the wall of the abdomen of the mother when the system 10 is worn.

The speakers 30 are connected to a sound generator 34, such as a conventional radio and tape player combination. The sound generator 34 could also adopt the form only of a tape player, a radio or the like. The sound generator could adopt any conventional form of sound generator and may be of the type described in my copending application Ser. No. 143,981, filed Nov. 11, 1993. The sound generator 34 may be any conventional type sound generator, as aforesaid, and may be fitted within a pocket 32 located on the belt 14 in the manner as shown. Otherwise, sound generators of this type may be conventionally provided with clips for clipping onto the belt 14.

Electrical conductors 36 are used to connect the speakers to the sound generator 34. However, when the sound generator is removed, it is necessary to disconnect the conductors 36. For this purpose, the conductors 36 exit the belt 14 at an exit port 37 and are provided with plugs 40 which literally plug into conventional sockets provided on the radio tape recorder unit. Thus, the sound generator 34 can be removed from the belt 14 and used for other purposes. Inasmuch as the details relating to the use of the invention for imparting sound have been described in my aforesaid co-pending application, those details may be incorporated herein by reference. Accordingly, they will be neither illustrated nor described in any further detail herein.

FIGS. 6–8 illustrate an embodiment of the invention which is used for the transmission of light radiation to the fetus. In many cases, if the light is of sufficient intensity, the light can penetrate, to some degree, the wall of the abdomen and even the uterus, to some degree. However, it has nevertheless been found that the light does have effects on the fetus.

One of the preferred forms of light sources which has been found to be effective for creating effects on the fetus are laser light sources. To some extent, this may be a result of the intensity of laser light sources, as well as a function of the wave length. As a simple example, with laser light, the beams of light are parallel much in the same manner as sunlight. Consequently, intensity can be quite substantial. Furthermore, even though the light is somewhat collimated, the light beam still does not carry a substantial amount of heat and, therefore, there is little or no damage to the abdomen tissue of the mother.

Some of the laser lights which can be used include the helium-neon lasers, and the helium-cadmium lasers. Also effective are many of the noble gas lasers and carbon dioxide lasers. Some laser mechanisms which could be used, but which have certain limitations because of power requirements, size and the like, include various chemical lasers, copper and gold vapor lasers, excimer lasers, far infrared gas lasers, and other commercial gas lasers. For that matter, some of the semi-conductor diode lasers, such as the short wavelength diode lasers and the long wavelength III–V semiconductor diode lasers can be used.

It has been recognized that digestion and assimilation by animals and humans are effected by light energy. Indeed, Albert Szent-Gyorgyi, Nobel prize winner and discoverer of vitamin C, has reported and recognized the effects of both light and even the color of light on the human body. Mr. Szent-Gyorgyi discovered that many enzymes and hormones of the body are involved in the processing of light energy and are sensitive to both the color and the intensity of light. These enzymes and hormones are actually stimulated by selected colors of light and undergo molecular changes which alter their original colors, and thereby cause dynamic reactions within the body. See Introduction to Sub-Molecular Biology, New York Academic Press 1960 by Albert Szent-Gyorgyi.

Although a fetus may not directly observe light, as such, because of the tissue between the source of light and the fetus, and also because of the fact that the eyesight of the fetus is not well developed, it has been recognized that the fetus will nevertheless detect the presence of light. The pineal gland apparently is sensitive to incidence of light on the body and acts as a type of light meter. Thus, it is established that the fetus is sensitive to incidence of light. It is for this reason that the pineal gland is often referred to as "the third eye".

Until recently, there was some scientific controversy over the effects of light on the human body, although science did recognize the effects of x-rays, ultraviolet rays and microwaves on the human body. However, the visible light differs from x-rays and other types of radiation only in wavelength range. Indeed, the various colors of light differ from one another only in wavelength range. It is now recognized that not only do the non-visible portions of the spectrum have effects on the human health, but also visible light has effects on the human health.

It is now known that lighting which simulates sunlight creates little or no stress on an individual and, moreover, it improves behavior and academic achievement. See H. Wohlfarth, et al. "The Effective of Color Pysicodynamic Environmental Modification Upon Physiological and Behavioral Reactions of Severely Handicapped Children" as reported in the International Journal of Biosocial Research, No. 3 (1982), pages 10–38. There are numerous reported cases where light has been used to cure mal-development or disease. Consequently, the applicant has recognized that light may have a very significant effect on the fetus.

In the present invention, a plurality of light sources 40. e.g. lights, are mounted on the interior face of the belt 14, as shown in FIGS. 4 and 8. These lights 40 may be any conventional type of incandescent light, although incandescent lights are not preferred due to the fact that they generate heat, if there is sufficient wattage for the required purpose. Fluorescent and neon lights are therefore preferred for this purpose and also they are more desirable since they consume less power for the same amount of light generation than do incandescent lights.

In the case of the present invention, the light sources may be within the visible wave length range. However, in some embodiments, the light sources may also be beyond the red or the violet light ranges, such as into the infrared or ultraviolet light ranges.

The light sources 40 are internally connected through electrical conductors 42 located within a plural ply-belt structure and with the wires connecting the light sources 40 extending between the plies of the belt, as hereinafter described in more detail. The conductors 42 exit the belt as shown in FIG. 8 and are connected to a suitable control unit 44 which is provided with control switches 46. The control unit may suitably contain conventional sequencers of the type which would cause a sequencing or strobing of the light to be imparted to the fetus. Otherwise, the control unit 44 may contain light-intensity controls and typical on/off controls.

It is has now been found that the noble gas lasers and carbon dioxide lasers are highly effective in creating the desired laser light. Moreover, the generators for producing this laser light can be made sufficiently small so as to be carried on a belt. Admittedly, energy level is still somewhat of a problem, although with a small rechargeable battery pack carried on the belt, effective laser operation can be achieved.

One preferred form of laser light which can be used in accordance with the present invention is that noble gas laser and which, in this case, uses a small metal-ceramic or ceramic tube. The current densities required for excitation calls for the discharge to be applied along the length of the laser tube and confined to a very narrow bore of 1–3 mm in diameter. A discharge current passes from the cathode in the tube along the narrow bore and collected at the anode. A linerally polarized light escapes without loss and serves as an optical path. In the case of the present invention, cooling, if needed, can be achieved by airflow. Moreover, a magnet which creates a magnetic field parallel to the bore axis may be used to help confine the discharge current to the center of the bore, thereby increasing the ion density.

Some of the noble gas lasers which can be used in accordance with the invention are the Crypton lasers and Argon lasers. Another laser which can be used in accordance with the present invention is a solid tube laser utilizing carbon dioxide. The tube is usually filled with carbon dioxide, helium and nitrogen and mirrors forming a resonate cavity are placed at the ends of the tube. Electrodes are located near the ends of the tube and the tube is filled with a proper gas and sealed. The voltage as applied to the electrodes causes a discharge through the gas. Again, air cooling is applied for dissipation of the generated heat.

One of the preferred light sources used in accordance with the present invention is the carbon dioxide laser light. It is a highly versatile type of light and emits infrared radiation between 9 and 11 micrometers and even at a single line which may be selected by the user. Moreover, it can be adapted to provide a continuous light output or a pulsed light output.

The laser used in accordance with the present invention is a sealed tube laser. In the embodiment as shown, the laser light employed uses a discharge tube 250 along with mirrors 252 at each of the opposite ends of the discharge tube 250. Connected to the discharge tube 250 is a relatively small gas supply reservoir 254 and a pump 256. The pump 256 can actually adopt the form of a fan. The gas supply reservoir 254 is provided with a fitting 258 for refilling the gas in the reservoir 254. Moreover, the entire assembly can be mounted in an outer housing 260 on the belt 16, as shown in FIG. 19.

In order to redirect any generated beam to the proper direction, a redirecting lens mechanism 262 is located at one end of the laser light housing 260. In this case, a pair of mirrors 252 in the redirecting mechanism 262 are shown in schematic form. In this way, a beam of light from an end of the housing would be redirected in a generally perpendicular path. However, any redirection mechanism could be employed for this purpose.

In addition to the foregoing, the discharge tube 250 is provided with a plurality of flutes or ribs 268 on its exterior surface. This enables some cooling to take place from the discharge tube.

In the preferred embodiment of the present invention, one of the mirrors 252 is a total reflecting mirror and the other of the mirrors 252 is a partially transparent mirror. The mirror close to the bean redirecting mechanism 262 is the partially transparent mirror, as shown in FIG. 20. The mirrors preferably are formed of silicon with a highly reflective coating, such as molybdenum and copper. Due to the fact that the gain is high in its carbon dioxide layer, the beam transmitted is higher than in the lower gain lasers, such as helium-neon.

The laser generated light unit is highly effective in that it can be packaged in a small compact unit and literally worn on a belt of a mother. This type of laser has been found to operate at room temperature and can function well in moderately clean environments. They are compact and the heads on the laser tube are only about one kilogram in weight. This type of laser light source is highly durable and generally fail proof in operation.

In order to achieve compactness, the discharge tube 250 could be constructed with a folded optic arrangement, as schematically shown in FIG. 21 of the drawings. In this case, an outer housing 280 is provided with longitudinal baffles 282 located therein. The baffles create a plurality of individual channels 284, including an upper channel and a lower channel, as shown. The mirror arrangements 286 are located at each of the ends of the channels, as shown. In this case, each mirror arrangement comprises a first mirror 288 located at approximately a 45° angle with respect to the light beam and which receives the light beam. A second mirror 290 receives the beam from the mirror 288 and is reflected to a generally reflecting mirror 292 to again redirect the light beam in a generally columnar path in the individual channels 284.

A generally first reflecting mirror 298 is located at one end of the upper channel and a partially reflecting and partially transparent mirror 294 is located adjacent the lower channel 284, as best shown in FIG. 21. The remaining construction of the laser, as shown in FIG. 21, is similar to that shown in FIG. 18. Again, it should be recognized that the outer housing 280 would also be provided with cooling fins or the like.

The control unit 44 is connected to a battery 48, through conductors 50, as also shown in FIGS. 6–8 of the drawings. In this way, electrical power is provided to the control unit 44 and hence, to the individual light sources 40. The control unit 44 is removably located within a suitable pocket 52 formed on the exterior surface of the belt, as best shown in FIGS. 7 and 8 of the drawings. In like manner, the conventional battery 48 is located within a pocket 54 also formed on the exterior of the belt 14, in the manner as shown in FIGS. 7 and 8 of the drawings. Preferably, the pocket 54 is closely located with respect to the pocket 52 so that conductors 50 extending between the battery 48 and the control unit 44 are relatively short in length. In accordance with the above-identified construction, both the control unit 44 and the battery 48 can be removed periodically for maintenance, recharging or for cleaning.

The battery 48 may be of a rechargeable type and for this purpose, it may be necessary to remove the battery 48 from the pocket 54. In like manner, the batteries may be replaceable batteries. If the batteries employed are small-sized dry cell batteries, then a casing inside the pocket 54 would be provided with an exterior plug for connection to the control unit 44. The conductors 50 are external conductors in the manner as shown. However, it should be understood that these conductors could extend within the belt and terminate with connectors inside of the respective pockets 52 and 54. The conductors 42 which exit the belt for connection to the control unit 44 are shown as being partially external. In like manner, they could exit the belt at the interior of the pocket 52 and also be provided with connectors for connection to the control unit 44.

As indicated previously, the various conductors could terminate inside of the pockets 52 and 54. In the same way, all conductors could have terminal connectors located within the pockets so that there are, in effect, no electrical conductors extending externally of the belt. In this way, the belt would provide a clean and attractive appearance and avoid the cumbersome problem of dealing with externally extending wires.

In the invention as illustrated thus far, the lights 40 have been shown as being mounted in a different belt than the sound generator and the speakers. In some embodiments of the invention, the lights may be provided without the speakers and sound generator and for this reason, have been illustrated in a separate belt. However, and in such cases, the sound generating system may be coupled with other sensory effects and, for that matter, the lights may be coupled with other sensory effects. Further, and more preferred embodiments, the lights will be included within the same belt as the sound generating equipment.

Also mounted in a pocket on the interior surface of the belt 14 is a sensor 64 which functions as a stethoscope sensor. Here again, the stethoscope sensor 64 is located close to the interior surface so that it is also disposed in juxtaposed relation to the wall of the abdomen of the mother. Further, a conductor 66 extends from the sensor 64 through the plies forming the belt 14 and terminates in a socket 68, as shown. The present invention provides a conventional stethoscope headset 70 for the mother to place in a position where the earpieces 72 are disposed in the ears of the mother. A cable 74 extends from the headset 70 and terminates in a plug 76 which is adapted for detachable connection to the socket 68.

In accordance with the above-identified construction, it can be observed that a user of this system can insert the earpieces 72 of the stethoscope 64 in her ear and connect the plug 76 to the socket 68. In this way, the headset 70 will be in sound conductive relationship with the stethoscope sensor 64.

When the mother desires to monitor the effect of sensory excitations, such as sound or light, on the fetal child, the mother can listen to the sounds from the abdomen itself. In this case, the mother may readily hear the heartbeat of the fetal child or otherwise, any physical activity such as kicking and the like. The mother is then in an excellent position to determine the effect of one type of light effect or sound effect upon the fetal child, compared to others. Thus, the mother can obtain that sound or light or other audio effects which are most soothing or enjoyable to the fetal child.

The embodiment of the system which utilizes sound is effective and relatively inexpensive, since it can use a conventional sound generator 34 and a conventional associated stethoscope arrangement as described in the aforesaid co-pending patent application. The embodiment of the invention which utilizes light is also highly effective and relative inexpensive, since it may also use conventional light sources and conventional batteries. The control unit 44 is generally made of conventional components, since off/on switches are well known and available as are sequencers and other elements which may be used to control the light. Consequently, there is no need to engage in expensive or elaborate modification of existing components. The systems, as described herein, are highly effective and achieve the desired results.

FIG. 9 illustrates an embodiment of the invention which uses a small electrical amplification system 80 for amplifying or otherwise attenuating the sounds generated by the stethoscope sensor. In this case, a stethoscope sensor 82, substantially identical to the previously described sensor 64, is mounted on the belt in substantially in the same position as the sensor 64. The output of the sensor 64 is introduced into a pizzo-electric crystal 84 for converting into an equivalent electrical signal. This electrical signal is then introduced into an operational amplifier 86 where the signal is amplified. In this respect, it should be understood that filters could also be employed for otherwise enhancing the sounds generated by the stethoscope sensor, if desired.

The output of the amplifier 86 is again introduced into another pizzo-electric crystal 88 for conversion back into sound. In this case, the output of the crystal 88, or similar electrical-sound converter, is connected to a coupling 90. The coupling 90 receives a plug 92 and which is connected through a sound tube 94 to a stethoscope headset 96. Thus, amplified sound is delivered directly to the stethoscope headset 96.

The sound amplification system, as illustrated in FIG. 9, is relatively simple, but is effective in amplifying the sounds of the fetus so that they can be more readily understood and heard by a mother who is relatively unexperienced with stethoscope sounds. The amplification system can be in the form of a small chip which can be mounted directly to the belt or otherwise, it can be included in a small compact unit which is affixed to the belt or retained in a pocket on the belt.

FIGS. 10 and 11 illustrate an embodiment of the invention which utilizes vibrators. In this case, conventional vibrators 100, such as the type used in hand-held vibration devices are mounted in the belt 14, as shown. The vibrator includes an outer plate 102 which is disposed against the abdomen wall of the mother, as well as motorized vibration generating mechanism, including a coil 104. The coil is connected through a pair of electrical conductors 106 to a battery source of power, such as the battery 48. In FIG. 10, a motor 110 is mounted on the exterior face of the belt 14 for operating the plate 102 of the vibrator. In this case, the motor 110 would be connected across the conductors 106, as shown. The vibrators, such as the vibrators 100, would also be connected to a control unit, such as the control unit 44. In this case, the control unit 44 would control the intensity of the vibration or the frequency of the vibration. Furthermore, the control unit 44 could be provided with individual controls to selective control any one or more of the individual vibrators.

FIG. 12 illustrates an embodiment in which magnets 120 may be mounted on the belt in place of the light sources 40 or in addition to the light sources. In this case, the magnets could be permanent magnets, although for purposes of control by the mother, they are preferably electromagnets. Since electromagnets are well known in the art, the operation of the electromagnets, per se, is not described in any further detail herein.

The electromagnets 120 are connected across a pair of conductors 122, as shown and which are in turn connected to a control unit 124. The control unit 124 could individually control the selected magnets which are to be energized or, for that matter, the intensity of the magnetic field which is generated. For this purpose, and when the magnets are electromagnets, a battery source of power 126, similar to the previously-described battery source of power 48, may be employed. The battery source of power 126 is connected to the control until 124 through conventional conductors 128.

If desired, and in order to create a magnetic field entirely across the abdomen of the mother, a metal plate 130 could be disposed behind the mother. This metal plate could be formed in the belt itself so as to couple magnetically with the magnets across the mother.

FIGS. 13 and 14 illustrate an embodiment of the invention in which heating plates 134 and 136 may be mounted within the belt 14, as shown. In FIG. 13, the plate 134 is located at the rear of the belt and in this case, is preferably designed to provide heat for purposes of relieving some of the back pain and tension encountered by the mother during the pregnancy. The forward heating plate 136 is either provided for the benefit of the mother or for the fetus, or both. In the embodiment as shown in FIG. 13, a pair of individual heating plates 136' and 136" are shown. It can be seen that these heating plates are mounted directly within the belt itself, and may extend to the surface of the belt. However, it is preferable to mount the heating plates in the belt with only a thin film of the leather, or other material forming the belt, extending over the heating plate to prevent direct contact of the heating plate with the skin of the mother. In this way, overheating or even burning to the mother's skin could be avoided.

Again, as with the other forms of sensory excitation, a heating unit is connected directly to a control unit 138 mounted within a pocket 140 retained on the belt. Again, for battery source of power, the control unit is connected to a battery 142 retained in a pocket 144 also mounted on the belt.

It should be understood that the light, sound, magnetic fields, vibration and heat are only some of the forms of sensory excitation which can be imparted to a fetus. Other forms could also be employed and with the proper transducer mounted directly on the belt 14. However, in all cases, the system of the invention is highly effective in that it allows the mother to easily monitor the effects of the sensory excitations on the fetus.

FIG. 15 illustrates an embodiment showing the belt 14 with speakers 30, lights 40 and vibrators 100 mounted within the belt, as shown. In addition, heating elements 136 are also shown as being mounted in the belt. In this embodiment, positional relationship of each of these aforesaid components for causing sensory excitation is actually shown where they may be mounted.

Also in the embodiment of the invention, as shown in FIG. 15, there is a single control unit 150 mounted within a pocket 152. The components are operated through the control unit utilizing power from a battery 154 also contained in a pocket 156 mounted on the battery. In this case, it can be seen that the control unit 150 is located at the side of the user and the battery pack could be moved slightly toward the back where it is somewhat in an out-of-the-way position.

These various components are relatively simple and utilize electrical conductors which are trained through the interior of the belt itself. Referring to FIG. 16, it can be seen that the speakers 30 are electrically connected by conductors

156 directly to a sound generator 158, such as a radio or tape player, or the like. The stethoscope sensor 64 is connected directly to the stethoscope tube, 66 as shown. The vibrators 100 and the lights 40 are both connected to a common pair of electrical conductors 160. These conductors are connected directly to the control unit 150 which is again, in turn, connected to the battery source of power 154, as shown. Thus, a simple pair of electrical conductors trained through the belt can operate the vibrators and lights, if both are employed. A separate pair of conductors trained through the belt will be connected to the sound generating unit. In like manner, if heating elements are employed, they could also be connected across the conductors 160. The same holds true of electromagnets and the like.

The actual belt may be provided with only a pair of pockets, one for the battery and one for the control unit, or it might be provided with a plurality of other pockets for holding additional control units or other equipment. The belt itself could also be constructed with a plurality of spaces for the addition of sensory excitation components. Thus, the user of the belt system could purchase an individual belt or harness arrangement and thereafter, at will, select additional components for use. The belt itself may be normally provided with internal conductors having leads terminating at pockets where the various sensory excitation transducers would be used. Thus, it would be a relatively simple procedure to install additional transducers if desired, or the additional equipment used to operate the transducers.

Also shown in FIG. 16 is an additional transducer 161 which is capable of monitoring another activity of the fetus, as for example, heart rate activity. Thus, the transducer 161 could function as a heart rate monitor. In this case, the transducer could also be connected across the conductors 160 if needed. A small chip which primarily functions as an amplifier 162 is connected to the transducer 161 and has an output conductor 164 connected to a jack terminal 166. In this way, the jack terminal 166 could be connected to a modem for transmitting fetal information directly to a physician or other attendant.

FIG. 17 illustrates one form of belt construction which may be used in the present invention. In this embodiment, the belt 14 is comprised of a pair of plies 170 and 172. Ply 170 is of a thicker cross-sectional construction than the ply 172 and is provided along a portion of its length with an interior cavity 174. This cavity is also provided with openings 176 to receive, for example, the speakers 30 and cavities 180 to receive the lights 40. It can be seen that the conductors, such as the electrical conductors 156, are trained right through the cavity 174. In like manner, the electrical conductors, such as the conductors 160 for operating lights and other equipment, are also located right in the cavity. In this way, simple cutout openings can be used to receive the transducers and with the conductors laid directly in the cavity 170. The second ply 172 can thereafter be secured to the interiorly presented face 182 of the ply 170.

In some cases the ply 172 can be releasably attached to the ply 170 so that the belt can be opened for the insertion of additional transducers or like equipment, or additional conductors In other cases, the plies could be permanently secured with conductors already laid in the cavity 174 and provided with terminal ends which can be grasped at the openings for connection to additional transducers.

As indicated previously, the system of the present invention also is capable of providing a sensory feedback and other types of feedback. In connection with the embodiment of the invention, as illustrated in FIG. 17, there was provided a built-in transducer 161 of the type which could function as a heart rate monitor and which had ultimately terminated with a jack terminal 166 for transmitting information via a modem.

FIG. 23 illustrates an embodiment of the invention utilizing the belt 14 and which also employs a transducer 190 connected to the belt through a conductor 192. In this case, the transducer 190 may be mounted on the belt or removably located in a pocket located within the belt but is removable therefrom. Thus, the transducer 190 could be located at various positions on the mother's abdomen in order to obtain fetal information or, for that matter, information about the mother.

The transducer 190 could adopt various forms as, for example, one which is capable of detecting acoustic information and immediately converting it into electrical signal form. Otherwise, the transducer 190 may be used as an acoustic transducer as, for example, in ultrasonic measurement and used for transmitting the acoustic information. Thus, the mother could obtain ultrasonic information about the fetus and ultimately transmit that information to a doctor or other practitioner who is capable of analyzing the information.

In FIG. 23, the cable 192 is shown as being extended through the belt 14 in the interior thereof as, for example, at reference numeral 194. This conductor is then connected to a suitable signal processing unit 196 located in a pocket 198 formed on the belt 14. Another conductor 200 terminating in a jack 202 for connection to a modem would be used for ultimately transmitting the measured information.

FIG. 24 illustrates an embodiment of the invention in which the transducer is capable of measuring data in acoustic format. For this purpose, the transducer 190 may adopt the form of an ultrasonic transducer. The cable 192 would also adopt the form of a cable capable of transmitting acoustic information as, for example, the type of cable used in a stethoscope. This sonic or ultrasonic information is then introduced into a filter 204 for filtering any extraneous signal or information which might have been detected during measurement.

The information, measured by the transducer 190, can be acoustically transmitted over a telephone link 206 comprised of a transmitting telephone 208 and a receiving telephone 210 via a telephone line 212. The information at the receiving telephone 210 is then ultimately converted by means of a suitable converter 214 into electrical format, much in the same manner as ultrasonic information is converted into an equivalent digital electrical format. This information is then capable of being stored in a computer 216 for processing or storage or display through a computer terminal 218.

The ultrasonic information which would normally be contained in a physician's office or in a hospital environment can be obtained directly from the mother and automatically processed for transmission via a telephone link to a physician's office or other attendant who would examine the received data. Thus, the belt of the present invention can become a much more sophisticated device for not only generating sensory effects for delivery to a fetus, but can also be used for measuring information about the fetus or about the mother and transmitting same for ultimate examination by an expert capable of analyzing the information.

FIG. 25 illustrates an embodiment of the invention in which information from the transducer 190 is used in electrical form. Thus, if the transducer 190 were capable of measuring data and providing an electrical signal representative of that data or, otherwise, provided with means for converting the data, that electrical data would first be amplified in an amplifier 224, as shown in FIG. 20 and thereafter transmitted to a conventional signal processing unit 226. The signal processing unit 226 can adopt a variety of forms, depending upon the actual type of signal which is to be processed and the required processing. For example, the signal may be in a wave form pattern which is to be rectified and consequently, the signal processing unit 226 would contain a suitable rectifier or the like. The signal processing unit may also include wave form clipping or the like.

The information from the signal processing unit 226 could be delivered to a modem 228 for transmission via a telephone link 230 comprised of a transmitting telephone 232, a receiving telephone 234 and a telephone line 236. Otherwise, a computer, or at least a signal display unit 238, may be interposed between the signal processing unit 226 and the modem 228. In this case, the computer 238 is shown as being provided with a display 240. Thus, the mother or other party at the location of the mother can also examine the data which is to be transmitted via the telephone link 230 by their own monitor 240.

The information which is transmitted from the modem 238 across the telephone link 230 would then be received by a remote modem 242 and then ultimately introduced into the storage of a computer 244. In this case, the computer 244 would similarly operate as a means for displaying the information on a computer display 246, or further processing the data or merely storing same.

In either of the aforesaid embodiments, as illustrated in FIGS. 24 and 25, it can be observed that the system of the present invention is also highly effective in measuring information about either the fetus or the mother, or both, and transmitting that information to a location where the information is to be analyzed. Consequently, and as indicated previously, the harness system, and particularly the belt 14, is not limited to mere generation of sensory excitation for delivery to a fetus or to a mother. The belt can also be used solely for the purpose of measuring and transmitting information, or may be used as a combination of both generating sensory excitation for the mother or fetus, or both, and for measuring data and transmitting the same.

Thus, there has been illustrated and described a unique and novel system for generating sensory excitations which can be imparted to a fetal child through a mother's abdomen and which thereby fulfills all of the objects and advantages which have been sought. It should be understood that many changes, modifications, variations and other uses and applications will become apparent to those skilled in the art after considering this specification and the accompanying drawings. Therefore, any and all such changes, modifications, variations and other uses and applications which do not depart form the spirit and scope of the invention are deemed to be covered by the invention.

Having thus described the invention, what I desire to claim and secure by Letters Patent is:

1. A system for the imparting of sensory excitations to a fetus cross the abdomen wall of the mother for stimulation of the fetus, said system comprising:

a) a belt sized to be worn about the waist region of a mother; and b) at least one light transmitting member mounted in and carried by said belt and being located in proximity to the abdomen and in proximity to that fetus for imparting light energy to the fetus across the wall of the abdomen; and c) light generating means carried by said belt and generating light of frequency and intensity so that the effects of the light can be imparted to said fetus and having an output connected to said light transmitting member to deliver the effects of the light to the fetus.

2. The system for imparting sensory excitation to a fetus of claim 1 further characterized in that said system comprises at least one other sensory excitation generating member carried by said belt and located in contact with the abdomen wall of the mother in proximity to the region of the fetus and generating excitations other than light in which the effects thereof are transmittable across the abdomen wall of the mother to thereby deliver such excitations to the fetus for purposes of stimulating the fetus, whereby the fetus receives the effects of at least light imparted across the abdomen and another sensory excitation across the abdomen.

3. The system of claim 1 further characterized in that a battery source of power is carried by or on said belt for energizing the light generating means.

4. The system of claim 2 further characterized in that a control means is associated with the light generating means to control same.

5. The system of claim 2 further characterized in that at least one other sensory excitation generating member is a sound generating transducer, a signal generating device is mounted on said belt, and electrical circuitry extending through said belt connects the transducer to the signal generating device.

6. The system of claim 5 further characterized in that a transducer of said light generating means is carried by said belt and is operatively located in proximity with the abdomen wall of the mother in proximity to the region of the fetus and is located in a pocket in said belt, and said light generating means is connected to a battery on said belt by conductors forming part of electrical circuitry extending through said belt.

7. A system for generating and imparting a sensory excitation to a fetal child through a mother's abdomen and which allows for monitoring effects on the fetal child, said system comprising:

a) a belt sized for wearing about the waist of a woman user and having a frontal portion which extends over a surface area of the lower abdomen of the woman user along with a back portion and connecting side portions;

b) at least one light generating transducer mounted on and carried by said belt and being located in juxtaposition to the abdomen in proximity to that fetal child for imparting effects of certain generated light to the fetal child across the wall of the abdomen;

c) at least one first pocket formed in said belt;

d) means associated with the light generating transducer and carried by said first pocket and generating light to be imparted to said fetal child;

e) a second pocket formed in said belt; and f) a stethoscope sensor fixedly and generally permanently mounted in and carried by said second pocket in said belt and also being located in juxtaposition to the abdomen in proximity to the fetal child to enable listening to sounds generated by the fetal child in the abdomen so that a user of the system can monitor the effects on the fetal child of the sensory excitations and which thereby enables the mother to control the sensory excitation until a desired response of the fetal child is detected.

8. The system of claim 7 further characterized in that a conductor extends from said stethoscope sensor internally through said belt and has a connector external to the belt in close proximity to the belt and is adapted to receive a second mating connector on the end of an earpiece conductor for coupling to said stethoscope sensor.

9. The system of claim 7 further characterized in that battery means is carried on said belt and an electrical conductor extending through said belt operates to connect the transducer to the battery means.

10. The system of claim 7 further characterized in that the belt has an enlarged frontal portion and an enlarged back portion relative to a side portion thereof, and where the frontal portion extends over a substantial surface area of the lower abdomen of the woman user.

11. The system for generating and imparting sensory excitations of claim 8 further characterized in that said system comprises a stethoscope headset comprising an earpiece for use by the woman user.

12. The system for generating and imparting sensory excitations of claim 11 further characterized in that the connector and the mating connector are adapted for quick release plug-in type connection.

13. The system of claim 12 further characterized in that the conductor extending from a connector to the earpiece is an electrical conductor and said earpiece comprises a speaker for reconverting an electrical signal into equivalent sensory excitations representing responses generated by the fetal child.

14. The system of claim 7 further characterized in that the generated light is light visible or non-visible to human beings and the transducer is a light source.

15. A method for generating and imparting various light energy sensory excitations to a fetal child in a pregnant woman's abdomen and which allows for monitoring effects on the fetal child, said method comprising:

a) extending a belt about the waist region of the pregnant woman;

b) locating a light generating transducer mounted on the belt in juxtaposition to the abdomen and in proximity to the fetal child;

c) generating effects of light as sensory excitations of a type to be imparted to the fetal child and imparting said excitations across the abdomen to the fetal child;

d) locating a stethoscope sensor within said belt in juxtaposition to the abdomen and in proximity to the fetal child;

e) locating an earpiece connected to said stethoscope sensor so that one can monitor the effects of the sensory excitations on the fetal child and listening to the sounds generated by the fetal child as a result of the application of the sensory excitations; and f) adjusting the sensory excitations to the fetal child in response to the monitoring of the effects on the fetal child to thereby provide sensory effects which are more comfortable to the fetal child.

16. The method of claim 15 in that said method comprises adjusting a control on a means for providing the sensory excitations to regulate same.

17. A system for employing light excitation to a fetus across the abdomen wall of the mother for stimulation of the fetus, said system comprising:

a) the belt sized to be worn about the waist region of a mother;

b) a laser light generating device mounted on said belt;

c) a gas supply also mounted on said belt and being connected across said laser light generating device;

d) pump means on said belt for pumping a gas supply in said laser light generating device; and e) means for redirecting the laser light through an opening in said belt and in contact with the abdomen wall of the mother for generating excitations across the abdomen wall of the mother to the fetus for purposes of stimulating the fetus.

18. The system of claim 17 further characterized in that a battery source of power is carried by said belt for energizing the laser light generating device.

19. The system of claim 17 further characterized in that said laser light generating member comprises an outer housing with baffles in said housing for forming a folded path of the laser light which is generated to thereby shorten the overall length of the housing.

20. The system of claim 18 further characterized in that conductors are carried through said belt from said battery source of power to said laser light generating member.

* * * * *